(12) United States Patent
Xu et al.

(10) Patent No.: US 12,084,425 B2
(45) Date of Patent: *Sep. 10, 2024

(54) METHOD FOR PREPARING ESCITALOPRAM BIS-HYDROXYNAPHTOATE CRYSTAL FORM A

(71) Applicants: ZHEJIANG HUAHAI PHARMACEUTICAL CO., LTD., Zhejiang (CN); SHANGHAI AOBO PHARMTECH, INC., LTD., Shanghai (CN)

(72) Inventors: Wei Xu, Shanghai (CN); Xi Chen, Shanghai (CN); Hong Gu, Shanghai (CN)

(73) Assignees: ZHEJIANG HUAHAI PHARMACEUTICAL CO., LTD, Zhejiang (CN); SHANGHAI AOBO PHARMTECH, INC., LTD., Shanghai (CN)

( * ) Notice: Subject to any disclaimer, the term of this patent is extended or adjusted under 35 U.S.C. 154(b) by 697 days.

This patent is subject to a terminal disclaimer.

(21) Appl. No.: 17/295,843

(22) PCT Filed: Oct. 12, 2019

(86) PCT No.: PCT/CN2019/110807
§ 371 (c)(1),
(2) Date: May 20, 2021

(87) PCT Pub. No.: WO2020/108117
PCT Pub. Date: Jun. 4, 2020

(65) Prior Publication Data
US 2021/0276968 A1    Sep. 9, 2021

(30) Foreign Application Priority Data
Nov. 26, 2018 (CN) .......................... 201811212608.5

(51) Int. Cl.
*C07D 307/87* (2006.01)

(52) U.S. Cl.
CPC ........ *C07D 307/87* (2013.01); *C07B 2200/13* (2013.01)

(58) Field of Classification Search
CPC .................................................... C07D 307/87
See application file for complete search history.

(56) References Cited

U.S. PATENT DOCUMENTS 4,943,590 A    7/1990    Boegesoe et al.
11,168,063 B2 *    11/2021    Xu ........................ C07D 307/87

FOREIGN PATENT DOCUMENTS

| CN | 102757414 A | 10/2012 |
| CN | 107311968 A | 11/2017 |
| CN | 108976188 A | 12/2018 |
| EP | 0347066 A1 | 12/1989 |
| WO | 2018171589 A1 | 9/2018 |
| WO | 2018223970 A1 | 12/2018 |

OTHER PUBLICATIONS

Office Action for Chinese Application No. 201980062665.6 dated Nov. 1, 20234; 7 pgs.

* cited by examiner

*Primary Examiner* — Bruck Kifle
(74) *Attorney, Agent, or Firm* — Umberg Zipser LLP

(57) ABSTRACT

Provided herein is a method for preparing an Escitalopram bis-hydroxynaphtoate ((S)-(+)-1-(3-(-(dimethylamino)propyl)-1-(4-fluorophenyl)-1,3-dihydro-5-cyanisob enzofuranone) crystal form A. Said method is ecofriendly and non pollutive, and the obtained Escitalopram bis-hydroxynaphtoate crystal form A is highly pure and easy to reproduce.

13 Claims, 3 Drawing Sheets

| Peak # | RetTime [min] | Type | Width [min] | Area [mAU*s] | Height [mAU] | Area % |
|---|---|---|---|---|---|---|
| 1 | 4.965 | MM | 0.1221 | 1.04446 | 1.88142e-1 | 3.327e-3 |
| 2 | 5.247 | MM | 0.1501 | 1.66857e4 | 1852.83008 | 53.1532 |
| 3 | 6.478 | MF | 0.1660 | 3.77522 | 3.78954e-1 | 0.0120 |
| 4 | 6.745 | FM | 0.1443 | 1.30746 | 1.51039e-1 | 4.165e-3 |
| 5 | 7.278 | MM | 0.2617 | 12.11539 | 7.71501e-1 | 0.0386 |
| 6 | 8.725 | MM | 0.3088 | 3.47771 | 1.87712e-1 | 0.0111 |
| 7 | 9.645 | MM | 0.3109 | 6.74968 | 3.61817e-1 | 0.0215 |
| 8 | 10.339 | MM R | 0.2178 | 1.46668e4 | 1122.51965 | 46.7219 |
| 9 | 11.205 | MM T | 0.0954 | 2.28069 | 3.98392e-1 | 7.265e-3 |
| 10 | 12.061 | MM | 0.1975 | 8.45872 | 7.13640e-1 | 0.0269 |

Fig. 3

METHOD FOR PREPARING ESCITALOPRAM BIS-HYDROXYNAPHTOATE CRYSTAL FORM A

The present application claims the priority of Chinese Patent Application No. 201811212608.5, entitled "A NEW PROCESS FOR PREPARING HIGH-PURITY ESCITALOPRAM PAMOATE", filed on Oct. 18, 2018 before China National Intellectual Property Administration, which is hereby incorporated by reference in its entirety.

FIELD OF INVENTION

The present application belongs to the technical field of medicine, and particularly relates to a method for preparing Escitalopram pamoate ((S)-(+)-1-(3-(dimethylamino)propyl)-1-(4-fluorophenyl)-1,3-dihydro-5-cyanoiso benzofuran pamoate) crystal form A.

BACKGROUND OF THE INVENTION

The chemical name of escitalopram is: (S)-(+)-1-(3-(-(dimethylamino)propyl)-1-(4-fluorophenyl)-1,3-dihydro-5-cyanoisobenzofuran. Escitalopram oxalate was developed jointly by U.S. Forest Laboratories, Inc. and Lundbeck Inc., Denmark. It was first launched in Euro-American countries such as Switzerland in March 2002 and approved by FDA in August 2002. Escitalopram, a serotonin reuptake inhibitor (SSRI), has a unique serotonin isomeric sites binding mechanism and is highly selective for serotonin receptors, thus being used for the treatment of major depression and the maintenance treatment of depression.

Patients with major depression are usually insubordinate, so it is difficult to evaluate whether a patient has received the accurate dose of the medicine or not. Thus, it is necessary to formulate escitalopram oxalate as a type of salt with low solubility and slow release by replacing acid radical.

The patent document EP0347066 discloses an escitalopram pamoate crystal form A and the preparation method thereof. The solvent used is methanol and the starting materials are escitalopram and pamoic acid.

Methanol, the solvent used in the above method for preparing escitalopram pamoate, has certain toxicity. Therefore, it is a technical problem to be solved for those skilled in the art to prepare escitalopram pamoate by using less toxic or even non-toxic solvent.

SUMMARY OF THE INVENTION

Through continuous research, the inventor of the present invention found a novel method for preparing escitalopram pamoate crystal form A by using water and ethanol as the solvent, thereby overcoming the problem of solvent toxicity in the prior art, the method is environment-friendly without pollution. Further, the escitalopram pamoate crystal form A prepared by the method has a purity over 99.5%.

Specific scheme is as follows:

The present invention provides a method for preparing an escitalopram pamoate crystal form A, comprising dissolving escitalopram oxalate in a reaction solvent to obtain an escitalopram oxalate solution; and adding a solution of a pamoate salt dropwise to precipitate escitalopram pamoate crystal form A

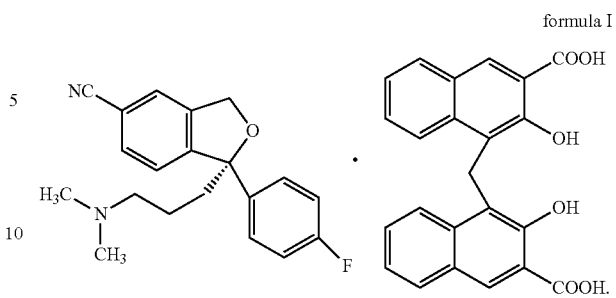

formula I

In some embodiments of the present invention, X-ray powder diffraction spectrum of crystal form A of the compound of formula I has characteristic peaks at 8.9±0.2°, 11.3±0.2°, 13.2±0.2°, 18.4±0.2°, 20.6±0.2° and 21.9±0.2°.

In some embodiments of the present invention, the reaction solvent is water.

In some embodiments of the present invention, dissolving is carried out at a temperature of 0-70° C.

In some embodiments of the present invention, dissolving is carried out at a temperature of is 25-35° C.

In some embodiments of the present invention, the pamoate salt is disodium pamoate.

In some embodiments of the present invention, a solvent of the pamoate salt solution is a mixed solvent of water and ethanol; preferably, a mixing ratio of water and ethanol in the mixed solvent is 7:3-3:7, preferably 1.2:1-1:1.2, more preperably 1:1.

In some embodiments of the present invention, during adding the solution of the pamoate salt dropwise, a temperature of escitalopram oxalate solution is 25-35° C.

In some embodiments of the present invention, during adding the solution of the pamoate salt dropwise, the temperature of escitalopram oxalate solution is 30° C.

In some embodiments of the present invention, a mass ratio of escitalopram oxalate and the pamoate salt is 1:0.9-1:1.2.

BRIEF DESCRIPTION OF THE DRAWINGS

In order to illustrate the examples of the present application and the technical solution of the prior art more clearly, the following is a brief description of the drawings that need to be used in the examples and the prior art. It is obvious that the drawings in the following description are only some of the examples of the present invention and according to these drawings, other drawings can be obtained by those skilled in the art without any inventive efforts.

FIG. 3 is the relevant datas of the HPLC spectrum of escitalopram pamoate crystal form A prepared according to Example 1.

DETAILED DESCRIPTION OF THE INVENTION

In order to make the technical problems, technical solutions and beneficial effects of the present application more clear, the application is further explained below in combination with specific examples. In the following examples, unless otherwise indicated, specific conditions of all of the test methods are generally carried out according to the conventional conditions or conditions recommended by manufacturers; raw materials and reagents are commercially available or prepared by using published information.

The data of X-ray powder diffraction used in the present application is determined by BRUKER D8 Advance from BRUKER Corp., Germany using Cu-Kα radiation; voltage and current: 40 kV, 40 mA; goniometer: Vertical goniometer, radius: 280 mm; slit: DS=2°, SS=1/2°, mask=15 mm, RS-5.0 mm; detector: LYNXEYE detector; scan patterns: continuous scan; scan range: 3-40°; count time per step: 0.2 s; total scan time: 390 s.

The HPLC detection conditions used in the present application are as follows:

| Instrument: | High performance liquid chromatograph equipped with an UV detector |
|---|---|
| Chromatographic column: | Waters Symmetry C18 100 × 4.6 mm, 3.5 μm |
| Mobile phase A | 3.54 g/L sodium hydrogen phosphate solution, pH is adjusted to 7.0 with phosphoric acid |
| Mobile phase B | Methanol: Acetonitrile = 1: 1 (V/V) |
| Mobile phase | Mobile phase A: Mobile phase B = 55: 45 (% V/V) |
| Detection wavelength: | 230 nm |
| Flow rate: | 1.2 mL/min |
| Sample size: | 10 μL |
| Column temperature: | 40° C. |
| Run time: | 25 min |

Figure 1:
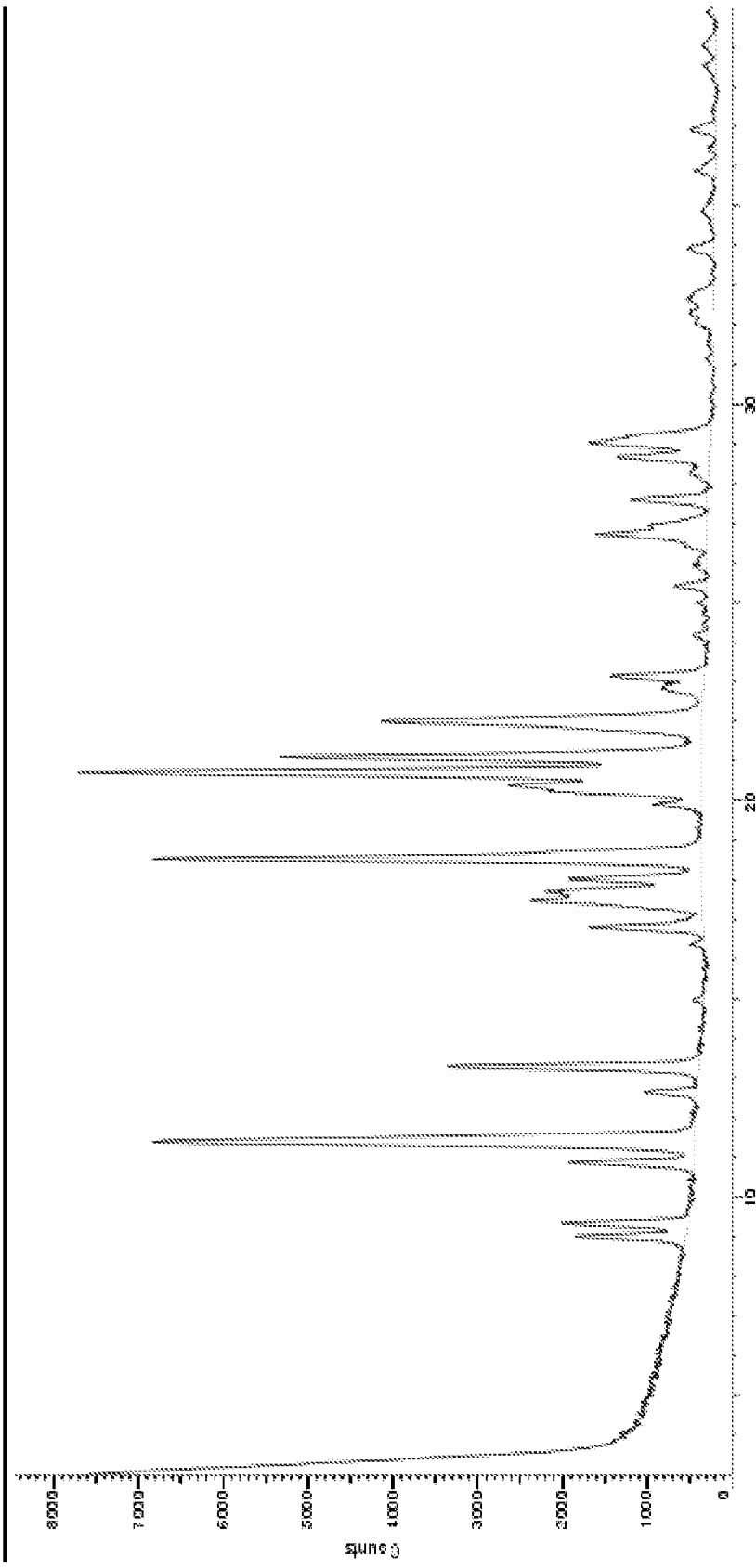
FIG. 1 is an XRPD spectrum of escitalopram pamoate crystal form A prepared according to Example 1.
Figure 2:
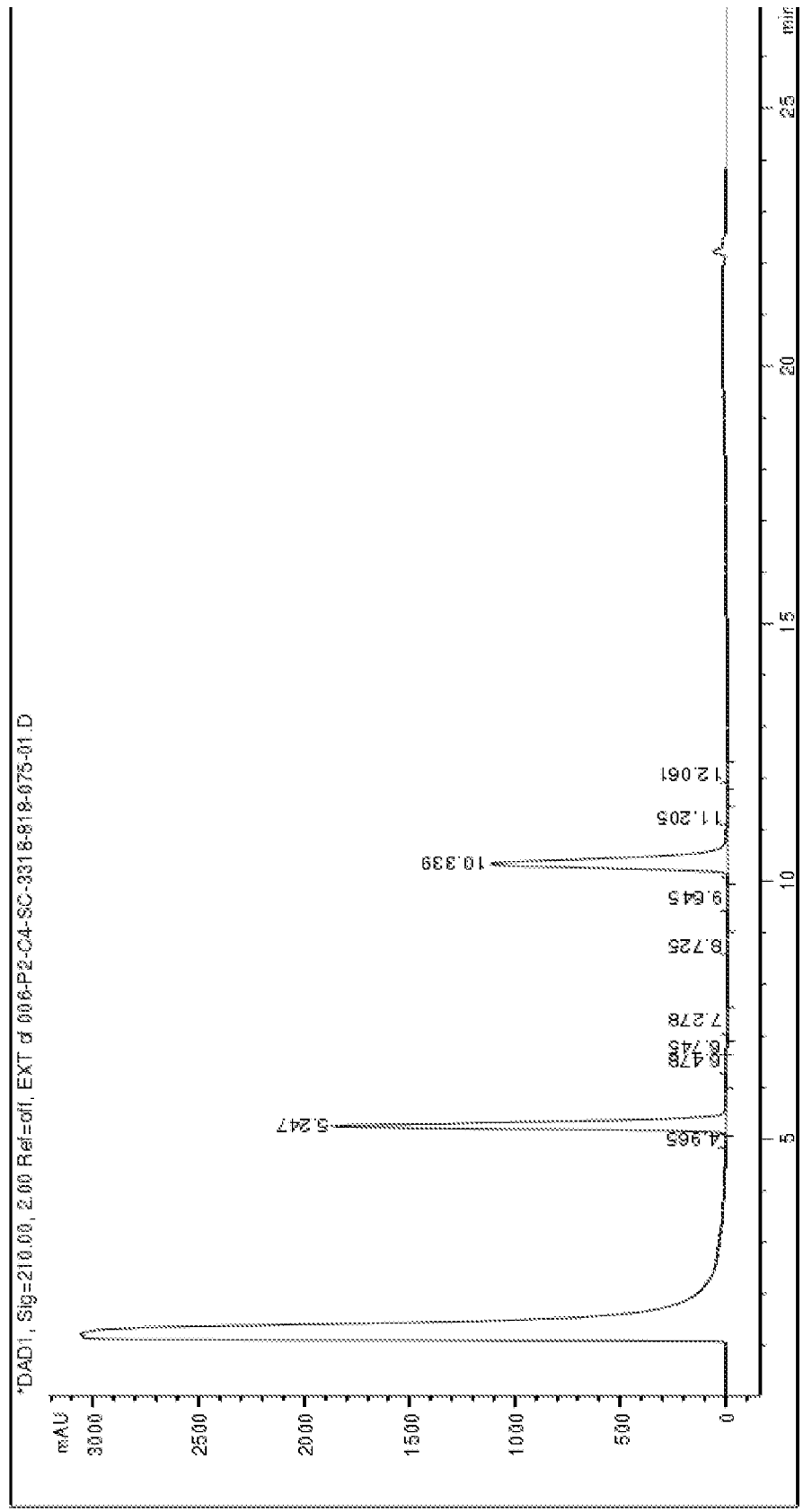
FIG. 2 is a HPLC spectrum of escitalopram pamoate crystal form A prepared according to Example 1.

Example 1: Preparation of Escitalopram Pamoate Crystal Form A 900 ml of water was added to 35 g of escitalopram oxalate sample, and was heated to 60° ° C. to completely dissolve it; 500 ml of water was added to 36.6 g of disodium pamoate to completely dissolve it at room temperature, then 500 ml of anhydrous ethanol was added and was mixed well. A water/ethanol mixed solution of disodium pamoate was added dropwise to escitalopram oxalate solution at 30° C. A solid was obtained immediately with good dispersion. After the addition was complete, the mixture was continuously stirred for 2 h and then filtered. The filter cake was washed with 500 ml of water, filtered with suction for 10 min and dried under vacuum. 59.5 g of escitalopram pamoate crystal form A sample was obtained. XRPD spectrum thereof was shown in FIG. 1; HPLC spectrum was shown in FIGS. 2 and 3; the purity was 99.87% by HPLC.

Example 2: Preparation of Escitalopram Pamoate Crystal Form A 25 ml of water was added to 500 mg of escitalopram oxalate sample, and was heated to 30° C. to completely dissolve it; 12.5 ml of water was added to 520 mg of disodium pamoate to completely dissolve it at room temperature, then 12.5 ml of anhydrous ethanol was added and was mixed well. A water/ethanol mixed solution of disodium pamoate was added dropwise to escitalopram oxalate solution at 30° C. A solid was obtained immediately with good dispersion. After the addition was complete, the mixture was continuously stirred for 2 h and then filtered. The filter cake was washed with 50 ml of water, filtered with suction for 10 min and dried under vacuum. 850 mg of escitalopram pamoate crystal form A was obtained. The purity was 99.86% by HPLC.

Example 3: Preparation of Escitalopram Pamoate Crystal Form A 140 ml of water was added to 5 g of escitalopram oxalate sample, and was heated to 60° C. to completely dissolve it; 25 ml of water was added to 5.2 g of disodium pamoate to completely dissolve it at room temperature, then 25 ml of anhydrous ethanol was added and was mixed well. A water/ethanol mixed solution of disodium pamoate was added dropwise to escitalopram oxalate solution at 30° C. A solid was obtained immediately with good dispersion. After the addition was complete, the mixture was continuously stirred for 2 h and then filtered. The filter cake was washed with 50 ml of water, filtered with suction for 10 min and dried under vacuum. 8.5 g of escitalopram pamoate crystal form A sample was obtained. The purity was 99.81% by HPLC.

Example 4

400 ml of water was added to 15 g of escitalopram oxalate sample, and was heated to 60° C. to completely dissolve it; 200 ml of water was added to 14.9 g of disodium pamoate, and then 120 ml of anhydrous ethanol was added and was mixed well. The solid was completely dissolved at room temperature. A water/ethanol mixed solution of disodium pamoate was added dropwise to escitalopram oxalate solution at 30° C. A solid was obtained immediately with slight agglomeration. After the addition was complete, the agglomeration was obvious. The mixture was continuously stirred for 2 h and then filtered. The filter cake was washed with 50 ml of water, filtered with suction for 10 min and dried under vacuum. 25.5 g of escitalopram pamoate crystal form A sample was obtained. The purity was 99.74% by HPLC.

Example 5

400 ml of water was added to 15 g of escitalopram oxalate sample, and was heated to 60° C. to completely dissolve it; 200 ml of water was added to 14.9 g of disodium pamoate, and then 100 ml of anhydrous ethanol was added and was mixed well. The solid was completely dissolved at room temperature. A water/ethanol mixed solution of disodium pamoate was added dropwise to escitalopram oxalate solution at 30° C. A solid was obtained immediately with relatively obvious agglomeration. After the addition was complete, the agglomeration was obvious. The mixture was continuously stirred for 2 h and then filtered. The filter cake was washed with 50 ml of water, filtered with suction for 10 min and dried under vacuum. 25.5 g of escitalopram pamoate crystal form A sample was obtained. The purity was 99.71% by HPLC.

Example 6

140 ml of water was added to 5 g of escitalopram oxalate sample, and was heated to 60° ° C. to completely dissolve it; 50 ml of water was added to 5.2 g of disodium pamoate to completely dissolve it at room temperature. Disodium pamoate solution was added dropwise to escitalopram oxalate solution at 30° C. A solid was obtained immediately with obvious agglomeration. After the addition was complete, the agglomeration was obvious. The mixture was continuously stirred for 2 h and then filtered. The filter cake was washed with 50 ml of water, filtered with suction for 10 min and dried under vacuum. 8.5 g of escitalopram pamoate crystal form A sample was obtained. The purity was 99.71% by HPLC.

The function of the above-mentioned examples is to explain the substantive content of the present application, it is not intended to limit the protection scope of the present application. Those skilled in the art should understand that the technical solutions of the present application can be modified or equivalently replaced without departing from the substance and protection scope of the technical solutions of the present application.

The invention claimed is:

1. A method for preparing a crystal form A of a compound of formula I, comprising:
dissolving escitalopram oxalate in a reaction solvent to obtain an escitalopram oxalate solution;
and adding a solution of a pamoate salt dropwise to precipitate the crystal form A of the compound of formula I

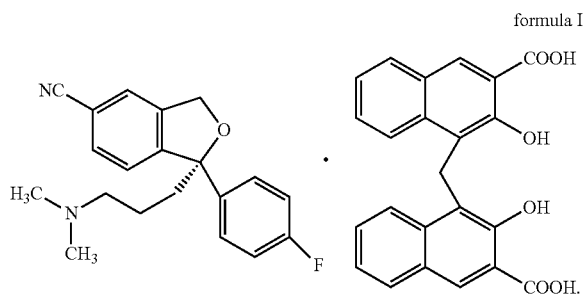

formula I

2. The method according to claim 1, wherein the reaction solvent is water.

3. The method according to claim 1, wherein dissolving is carried out at a temperature of 0-70° C.

4. The method according to claim 3, wherein dissolving is carried out at a temperature of 25-35° C.

5. The method according to claim 1, wherein the pamoate salt is disodium pamoate.

6. The method according to claim 1, wherein a solvent of the solution of the pamoate salt is a mixed solvent of water and ethanol.

7. The method according to claim 6, wherein a volume ratio of water and ethanol in the mixed solvent is 7:3-3:7.

8. The method according to claim 1, wherein during adding the solution of the pamoate salt dropwise, a temperature of the escitalopram oxalate solution is 25-35° C.

9. The method according to claim 8, wherein during adding the solution of the pamoate salt dropwise, the temperature of the escitalopram oxalate solution is 30° C.

10. The method according to claim 1, wherein a mass ratio of escitalopram oxalate and the pamoate salt is 1:0.9-1:1.2.

11. The method according to claim 1, wherein the crystal form A of the compound of formula I has a X-ray powder diffraction spectrum, showing characteristic peaks at 8.9±0.2°, 11.3±0.2°, 13.2±0.2°, 18.4±0.2°, 20.6±0.2° and 21.9±0.2°.

12. The method according to claim 6, wherein a volume ratio of water and ethanol in the mixed solvent is 1.2:1-1:1.2.

13. The method according to claim 6, wherein a volume ratio of water and ethanol in the mixed solvent is 1:1.

* * * * *